United States Patent [19]
Corby, Jr.

[11] Patent Number: 5,274,551
[45] Date of Patent: Dec. 28, 1993

[54] METHOD AND APPARATUS FOR REAL-TIME NAVIGATION ASSIST IN INTERVENTIONAL RADIOLOGICAL PROCEDURES

[75] Inventor: Nelson R. Corby, Jr., Scotia, N.Y.

[73] Assignee: General Electric Company, Schenectady, N.Y.

[21] Appl. No.: 800,374

[22] Filed: Nov. 29, 1991

[51] Int. Cl.$^5$ .......................... G06F 15/00; A61B 6/00
[52] U.S. Cl. ................... 364/413.13; 128/654; 128/656; 358/88
[58] Field of Search ...................... 364/413.13; 358/88, 358/98; 382/6, 33, 55, 16, 46, 51; 128/654–658

[56] References Cited

U.S. PATENT DOCUMENTS

| | | | |
|---|---|---|---|
| 4,459,990 | 7/1984 | Barnea ................................. | 128/656 |
| 4,680,709 | 7/1987 | Srinivasan et al. ..................... | 382/6 |
| 4,922,332 | 5/1990 | Taniguchi et al. ..................... | 358/77 |
| 4,998,972 | 3/1991 | Chin et al. ............................ | 128/6 |
| 5,036,464 | 7/1991 | Gillica et al. ..................... | 364/413.13 |
| 5,119,445 | 6/1992 | Suzuki et al. ........................ | 382/55 |

OTHER PUBLICATIONS

Thesis–Three Dimensional Navigation Assist for Interventional Radiological Procedures, submitted to the Graduate Faculty of Rensselaer Polytechnic Institute on Dec. 1990, Jonathan A. Zarge.

*Primary Examiner*—Roy N. Envall, Jr.
*Assistant Examiner*—Frantzy Poinvil
*Attorney, Agent, or Firm*—Paul R. Webb, II

[57] ABSTRACT

An integrated system for real-time navigation assist during interventional radiological procedures utilizes a two-dimensional model of a catheter guide wire, obtained by performing image analysis on a fluoroscopic image in realtime, and a three-dimensional model of a patient's vascular system. The system backprojects the two-dimensional model into the three dimensional model and provides a three-dimensional display of the catheter in a patient's vascular system in real-time.

12 Claims, 13 Drawing Sheets fig. 15
```
V         9 10 16
V         9 10 11 12
V         9 10 11 13 14
V         9 10 11 13 15 17
V         9 10 11 13 18
V    2 4 5 8 10 16
V    2 4 5 8 10 11 12
V    2 4 5 8 10 11 13 14
V    2 4 5 8 10 11 13 15 17
V    2 4 5 8 10 11 13 18
V    1 4 5 8 10 16

···   (18 PATHS OMITTED)   ···

V    7 5 8 10 16

V         3 1 2 6 5
I         3 1 2 6 4 3
I         3 1 2 6 4 1
V         3 1 2 7 8 9 10 12
V         3 1 2 7 8 9 10 11
V         3 1 2 7 8 11 12
V         3 1 2 7 8 10 9
V         3 1 2 7 9 8 10 12
V         3 1 2 7 9 8 10 11
V         3 1 2 7 9 11 12
V         3 1 2 7 9 1 10 9
V         3 1 2 7 10 12
V         3 1 2 7 10 11 8
V         3 1 2 7 10 11 9
I      5 4 1 2 6 5
I      5 4 1 2 6 4 3
I      5 4 1 2 6 4 1
V      5 4 1 2 6 8 9 10 12

···   (163 PATHS OMITTED)   ···

I  9 11 10 7 6 4 1 2 7 10 11 9
```

METHOD AND APPARATUS FOR REAL-TIME NAVIGATION ASSIST IN INTERVENTIONAL RADIOLOGICAL PROCEDURES

This invention relates generally to the field of Interventional Radiological procedures and more specifically to a system for providing the physician performing the procedure with a real-time indication of the location of a catheter within a three-dimensional model of a patient's vascular system.

RELATED APPLICATIONS

The present application is related to commonly assigned and copending U.S. patent application Ser. Nos. 07/800,379 and 07/800,377 entitled respectively, A Method for Reducing X-Ray Dosage During Fluoroscopic Examinations and Method and Apparatus for Real-Time Tracking of Catheter Guide Wires in Fluoroscopic Images During Interventional Radiological Procedures both filed Nov. 29, 1991.

BACKGROUND OF THE INVENTION

Interventional Radiology (IR) is a rapidly growing branch of medicine which uses medical imaging systems such as Computer Tomography, Magnetic Resonance, X-ray and fluoroscopy for therapeutic as well as diagnostic purposes. In IR, a physician wishes to guide a catheter to a remote site within the body for the purpose of making measurements, retrieving samples (biopsy), effecting therapeutic actions (for example, angioplasty of an artery wall), or blocking of an artery feeding a tumor (embolization). The catheter is a thin tube (2-6 mm diameter) on the order of 1 meter long which contains a number of interior passages (depending on design) and which is guided by a flexible, removeable, radio opaque internal guide wire.

The circulatory system can be thought of as a tree-like structure fanning out from a central arterial tube at the heart. The diameter of the main aorta is on the order of 2-4 cm. Beginning with the bifurcation of the main aorta, each subsequent branch forks or bifurcates into two or more smaller diameter branches Eventually at the cellular level the arterial diameter narrows to that of an individual red blood cell. The veinous system is responsible for collecting the blood cells from the capillaries for eventual return to the heart. The geometry of the veinous network is the inverse of the arterial system, with small tubes merging to form larger tubes which merge to form still larger tubes. While there is considerable similarity in topology and geometry among individuals at a gross level, at a detailed level the vascular system has a complex topology with a tortuous three-dimensional geometry which is unique to each individual.

The goal of an IR procedure is to deliver the working end of a catheter to an internal site within the body of the patient. The vascular system is used to physically contain the catheter and to act as the conduit along which the catheter progresses. Access to the vascular system is via a puncture with a tubular sleeve which remains in place during the procedure. The catheter and guide wire are threaded through the sleeve.

The fluoroscope (a 30 Hz X-ray machine) is the primary tool used by the physician to help guide the catheter. In many cases, his knowledge of general vascular anatomy, his experience, and the "in-process" fluoroscope images provide sufficient information to enable the physician to reach the target site. Typically, fluoroscope images are formed at a rate of 30 per second and displayed on a TV-like monitor. In order to see the local structure of the vascular system in the vicinity of the catheter tip more clearly, the physician injects a radio opaque dye into the catheter As the dye flows from the end of the catheter into the bloodstream, it temporarily renders the vein or arter opaque, causing the vessel to become a silhouette on the fluoroscope monitor. Depending on the amount of dye introduced, the rate at which it is introduced, and the blood flow rate, the opacification lasts from 2-5 seconds. As new blood arrives, the dye is diluted and swept away and the opacification gradually fades. This procedure can be very uncomfortable for the patient since the dye causes a burning sensation as it enters the bloodstream.

The sites that are particularly well suited to IR-based treatments lie further along the vascular "highway". For these situations the physician acquires what is called a "roadmap". For example, if the goal is to thread a catheter to a site deep within the kidney, the physician would first guide the catheter tip to the vicinity of the main artery feeding the kidney. A large enough amount of dye is introduced to opacify most or all arteries within the organ. As the dye is introduced, the fluoroscope is turned on and runs during the next 10-20 seconds. The images are stored for replay after the dye injection. After dye injection, the images are reviewed and the most representative image is transferred to a display monitor to be used as a two-dimensional reference image for the actual therapeutic procedure. Unfortunately the reference image or roadmap image is only a two-dimensional projection of the complex three-dimensional anatomy of the patient. Many systems in use allow the physician to subtract this roadmap from the live fluoroscopic image; in this mode the roadmap image acts as a mask which removes the background, non-vascular tissue (usually bones) and highlights the opacified vessels and catheter guide wire in the subtracted output image. Since the bones in the image remain constant in both the raw image and the roadmap image, when the images are subtracted, the bones disappear, the catheter guide wire remains black, and the opacified vessels become white. It usually takes multiple dye injections for the physician to reach the desired body location:

The next step is to guide the catheter ("avigate") to the desired site within the organ. The physician does this by viewing the fluoroscope image and referring to the two-dimensional roadmap image. He advances the catheter tip slightly, injects a small amount of dye into the catheter, observes the locally opacified arteries, compares the real-time image to the static roadmap image and determine if he is "on-course". If the vascular network lies largely in a plane that is perpendicular to the imaging axis, then the navigation is not difficult. Unfortunately, most of the vasculature at the organ level is of small diameter and twists and turns in a complicated way in three dimensions. In these cases, the two-dimensional roadmap and the two-dimensional real-time fluoroscope images can be very confusing. Choosing the correct pathway can become a time consuming trial and error procedure as the physician injects dye and attempts to interpret the imagery. In many cases, the only recourse is to physically rotate the imaging axis with respect to the patient to gain a view from another perspective. This is called "angulating" the fluoroscope. In many cases, it may be necessary to angulate and inject a number of times as the physician attempts to "make sense" of the projected roadmap image.

What is needed is a three-dimensional roadmapping and real-time guidance system that is analogous to the current two-dimensional system.

SUMMARY OF THE INVENTION

In accordance with the present invention, there is provided a method and apparatus that allows a physician to more rapidly guide a catheter through the circulatory system of a patient undergoing a diagnostic or therapeutic Interventional Radiological (IR) procedure by providing a three-dimensional visual representation of the position and orientation of the catheter with respect to the vasculature of the patient.

The method and apparatus use a topologically correct and geometrically accurate three-dimensional "map" of a specific patient's vascular system from diagnostic images produced by diagnostic imaging apparatus such as CT scanners, MR scanners or ordinary X-ray imaging systems. The instantaneous position and orientation of the catheter within the patient's vascular system is derived from analysis of "real-time" imaging sources, such as fluoroscope, with reference to the above mentioned map data. A special display processor merges the map data and catheter position data in real-time and produces a navigation display on an operating room monitor for use by the physician as he manipulates and advances the catheter. Preferably, the display is equipped with an operator interface which allows the physician to obtain varying views of the vascular model.

BRIEF DESCRIPTION OF DRAWINGS

FIG. 15 illustrates paths derived from a simple test image and a complex test image.

DESCRIPTION OF THE INVENTION

Figure 1:
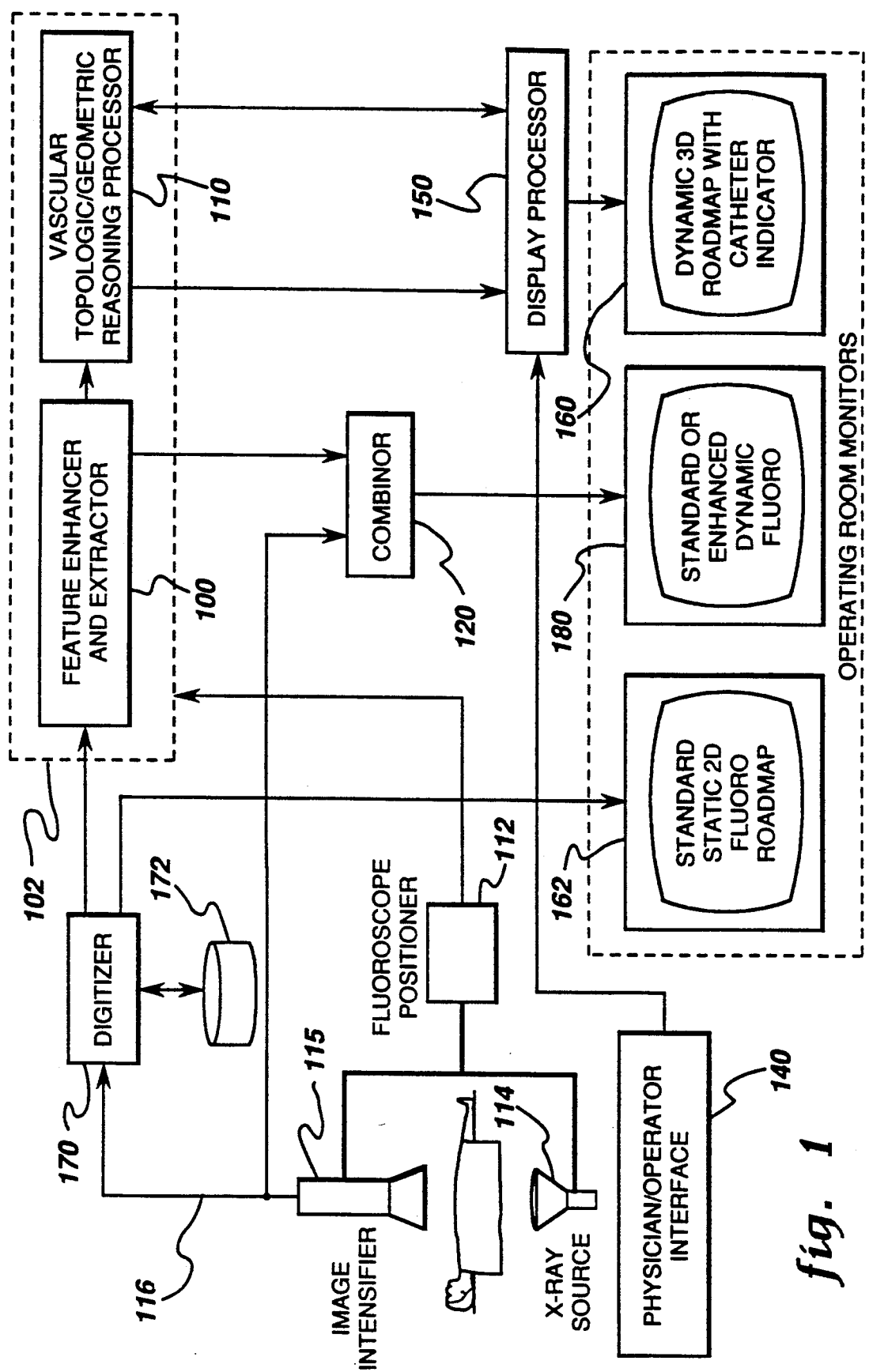
FIG. 1 is a block diagram of the navigation assist apparatus of the present invention.

Turning now to FIG. 1, there is shown an X-ray source 114 positioned below a patent undergoing an interventional radiological (IR) procedure. An image intensifier 115, such as would be part of a standard fluoroscope, produces video signals 116 which are then digitized by digitizer 170 and stored in frame storage device 172. A fluoroscope positioner 112 provides information on the position of the fluoroscope relative to the patient being imaged. As will be seen below, this information is needed later in the process to map a two-dimensional image to a three-dimensional model. The images stored at storage device 172 consist of 640 horizontal pixels and 484 vertical pixels. Each pixel typically has a value between 0 and 255 (0=black, 255=white). Digitized images stored in storage device 172 can be displayed on display device 162 to provide an attending physician with the "roadmap" image described in the background section of the present application. The digitized images from digitizer 170 are transmitted to a digital computer 102 which has a feature enhancer and extractor 100 at the same rate that the image stream is produced by the image intensifier 115 (typically 30 per second). Image enhancer and extractor 100 analyzes the digitized images and extracts the pixels from the image corresponding to a catheter in the image. The output of the feature enhancer and extractor is a two-dimensional model of the catheter. The model serves as input to the vascular topologic geometric reasoning processor 110. Processor 110 computes the three-dimensional location of the catheter from the two-dimensional model.

The display subsystem, consisting of 162, 180, and 160 in FIG. 1 is used for manipulation feedback to the physician as he attempts to guide the catheter and guide wire. The navigation display 160 is added to the standard set of TV-like displays positioned in front of the physician in the operating room. Ideally, the display would be a true three-dimensional representation or rendering of the patient-specific three-dimensional vascular map in either iconic or schematic form with a catheter icon or indicator superimposed on or merged with the vascular map. The composite image would be updated regularly and rapidly (possible 30 to 60 times a second) and would serve as an instantaneous indicator of the exact position and orientation of the catheter relative to the patient's vascular system.

The display would be interactively tied to the physician through an operators interface that would allow the display to be varied to suit the needs of the physician. Typical requirements would be viewpoint change, magnification, and translation. A benefit from such a system would be a method of highlighting the catheter guide wire in a standard fluoroscope output. Often the catheter becomes difficult to differentiate in the fluoroscopic image due to the amount of tissue through which the X-rays must penetrate. This invention could be used to display catheter guide wire pixels (or two-dimensional guide wire models) overlayed on the raw fluoroscopic image, as a further aid to the radiologist. This is shown in FIG. 1. The combinor 120 is a switch which can alternate between providing a standard fluoroscope signal and the catheter location information which can be highlighted on the display 180.

Figure 2:
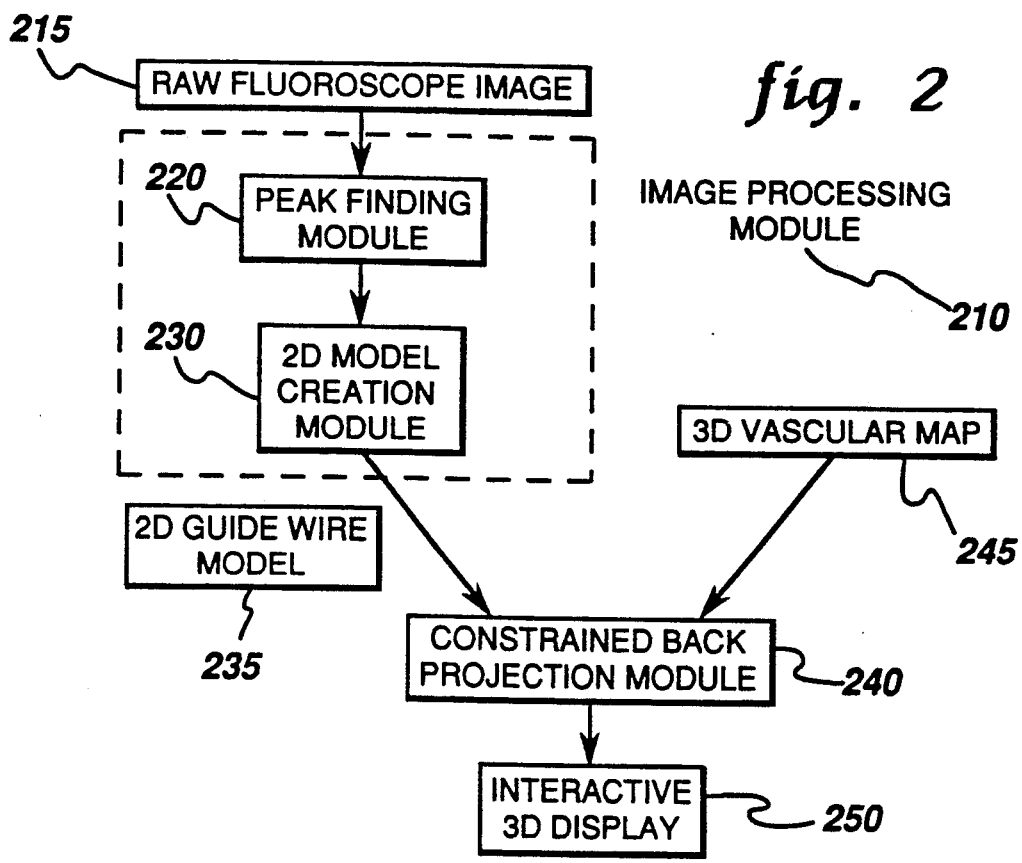
FIG. 2 is an apparatus design diagram showing the interaction of the image processing and backprojection modules.

FIG. 2 shows in greater detail the function of block 102 in FIG. 1. The image processing module 210 extracts a two-dimensional catheter model from a digitized fluoroscope image 215. This process is broken up into two parts, peak finding 220 and two-dimensional model creation 230. Peak finding module 220 determines which pixels (two-dimensional picture elements) in the images correspond to the catheter guide wire.

Two-dimensional model creation module 230 scans these pixels for connectivity to other guide wire pixels which eventually results in a two-dimensional model 235 (linked list of pixels) of the catheter guide wire in the image plane. Constrained backprojection module 240 computes the three-dimensional location of the catheter in the vascular map 245 and it is displayed on display 250.

Figure 3:
FIG. 3 is a sample fluoroscopic image.

FIG. 3 shows a sample fluoroscopic image of a catheter. This image is a lateral view of a head facing right (note the teeth in the lower right hand corner). The thin black line is the shadow of the catheter guide wire in the image plane. The continuous chain of pixels in the center of this black line is the target pixel chain for the peak finding module. The guide wire pixels have certain characteristics that facilitate finding them in an image. First, all the guide wire pixels have relatively low values. Since this guide wire is narrow, it has a high spatial frequency across the wire; in other words, the guide wire is the "sharpest" feature in the image. Finally, all of the guide wire pixels are adjacent to each other unless the guide wire's opacification is not continuous.

Figure 4:
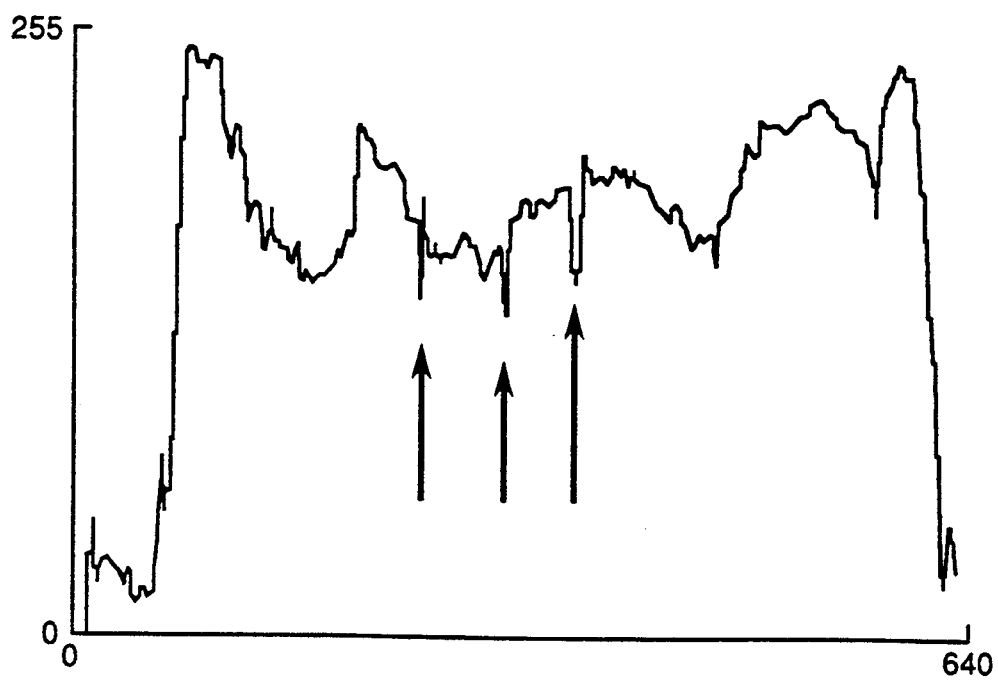
FIG. 4 is a graph showing intensity values for the sample image.

FIG. 4 is a graph of the pixel values across a horizontal line through the middle of the fluoroscopic image of FIG. 3. The guide wire pixels correspond to the bottom of the deep, steep valleys in the graph (indicated by the arrows).

Figure 5:
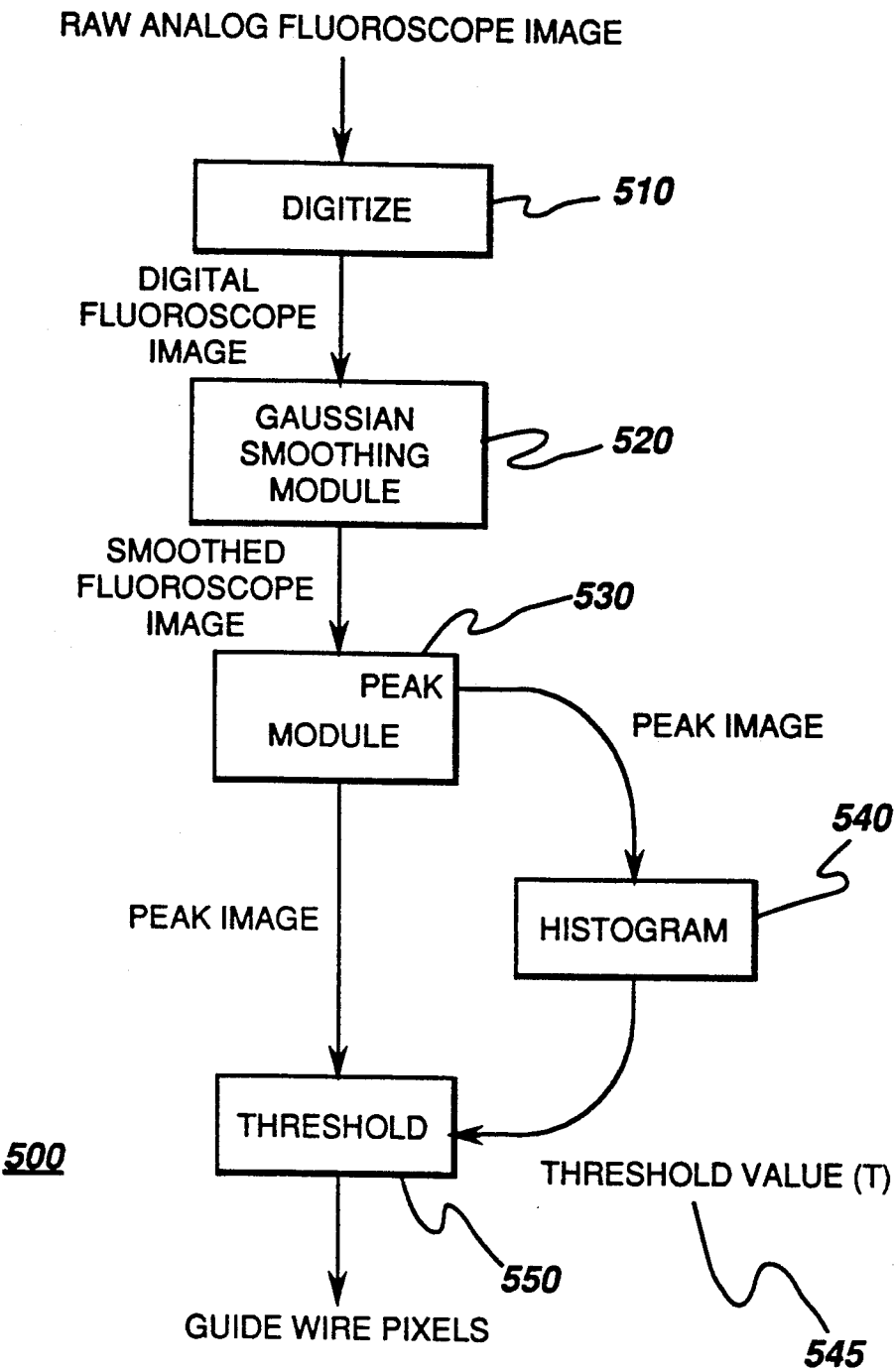
FIG. 5 is a peak image histogram for the sample image.

FIG. 5 shows the algorithm used to locate the catheter guide wire pixels. First the image is digitized at block 510. Next, the image is smoothed with a 5×5 Guassian kernal at block 520. Second derivative values for each pixel are computed in the four principle directions; horizontal, vertical, and the two diagonals. Rotated variations of [1−2 1] are used. The [1 −2 1] kernals implement the second derivative operation. The peak module 430 converts a raw image into a peak image. For every pixel P in the image, the maximum of the four second derivatives is computed by convolving the image with the kernals described above and taking the maximum of those four values Next, each pixel is tested to determine if it is a maximal gradient point in the direction from which the maximal value was discovered. If it is, the value of pixel P is set to that maximal value, if not, P is set to a low value (lower than any of the maximal gradient values). The resulting image is a peak image of the original raw fluoroscopic image.

Figure 6:
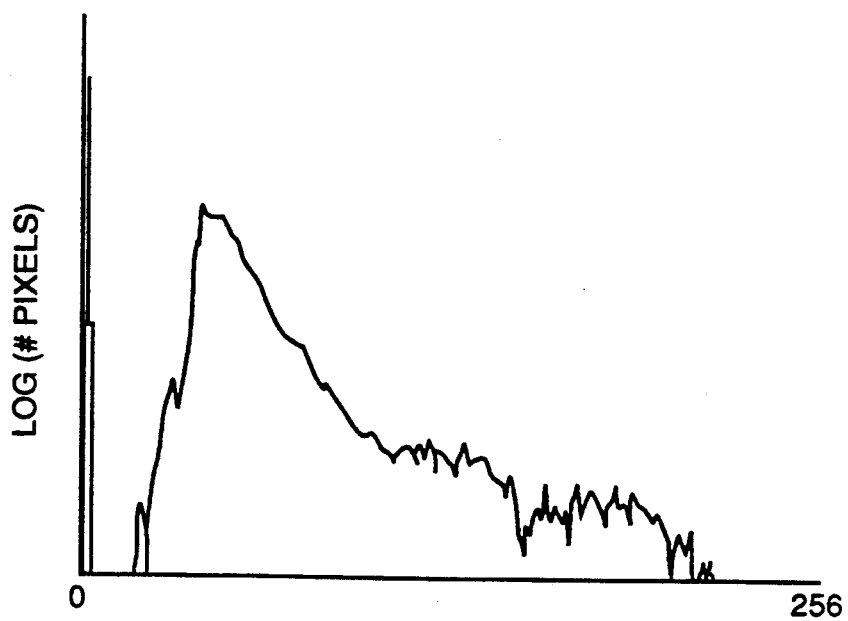
FIG. 6 is the output of the peak filter algorithm on the sample image.
Figure 7:
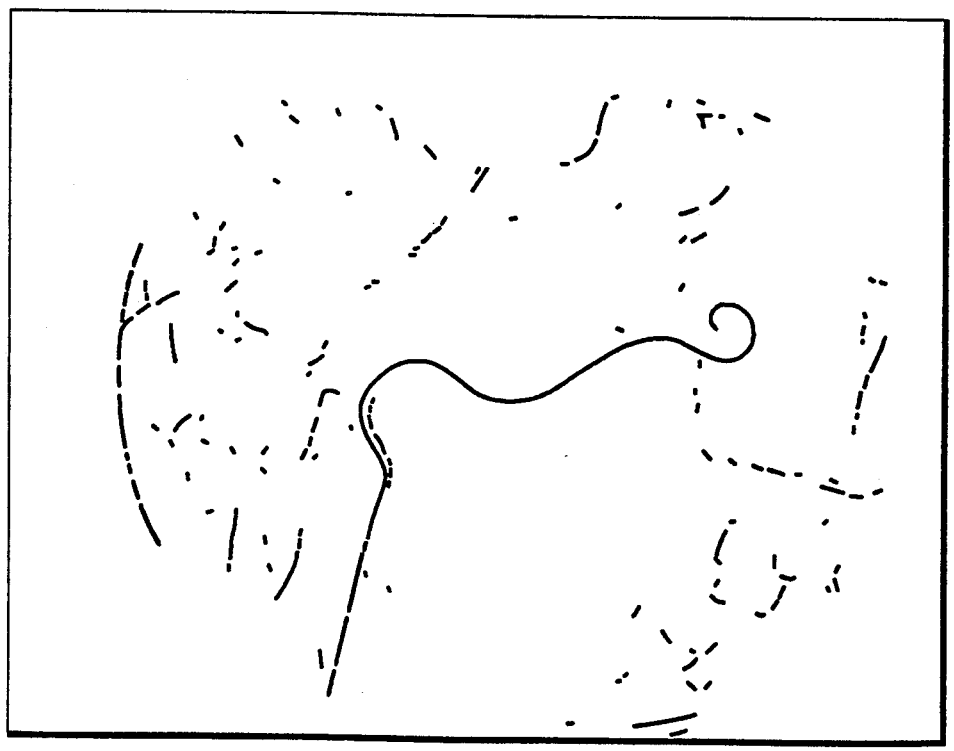
FIG. 7 is a system design diagram for the image processing module.

The next step 550 is to find the proper threshold value for the peak image. For this, a histogram 540 is necessary. FIG. 6 shows the histogram of the peak image of the sample image in FIG. 3. The histogram reveals that there is a large spike of pixels whose value is at the low end of the range. In FIG. 6, this spike is adjacent to the vertical axis of the graph. Besides this spike at the minimum value, a more "normal" distribution of values exists over the remaining values in the peak image. Before the threshold value is computed, the image is masked to blank out all pixels near the edge of the image and outside of the circular region that defines the boundary of the fluoroscope data. Then, the proper threshold, T (545 in FIG. 5), is computed based on the histogram of the peak image data. In a preferred implementation, T is set to the mean plus two standard deviations (the mean and standard deviation for the peak image are computed based on peak image pixel values except those pixels whose value is at the minimum spike). FIG. 6 shows the resulting binary image. There are small breaks in the guide wire pixel chains but this problem will be discussed and solved hereinbelow. This binary peak image is the input for the two-dimensional model creation module.

Figure 8:
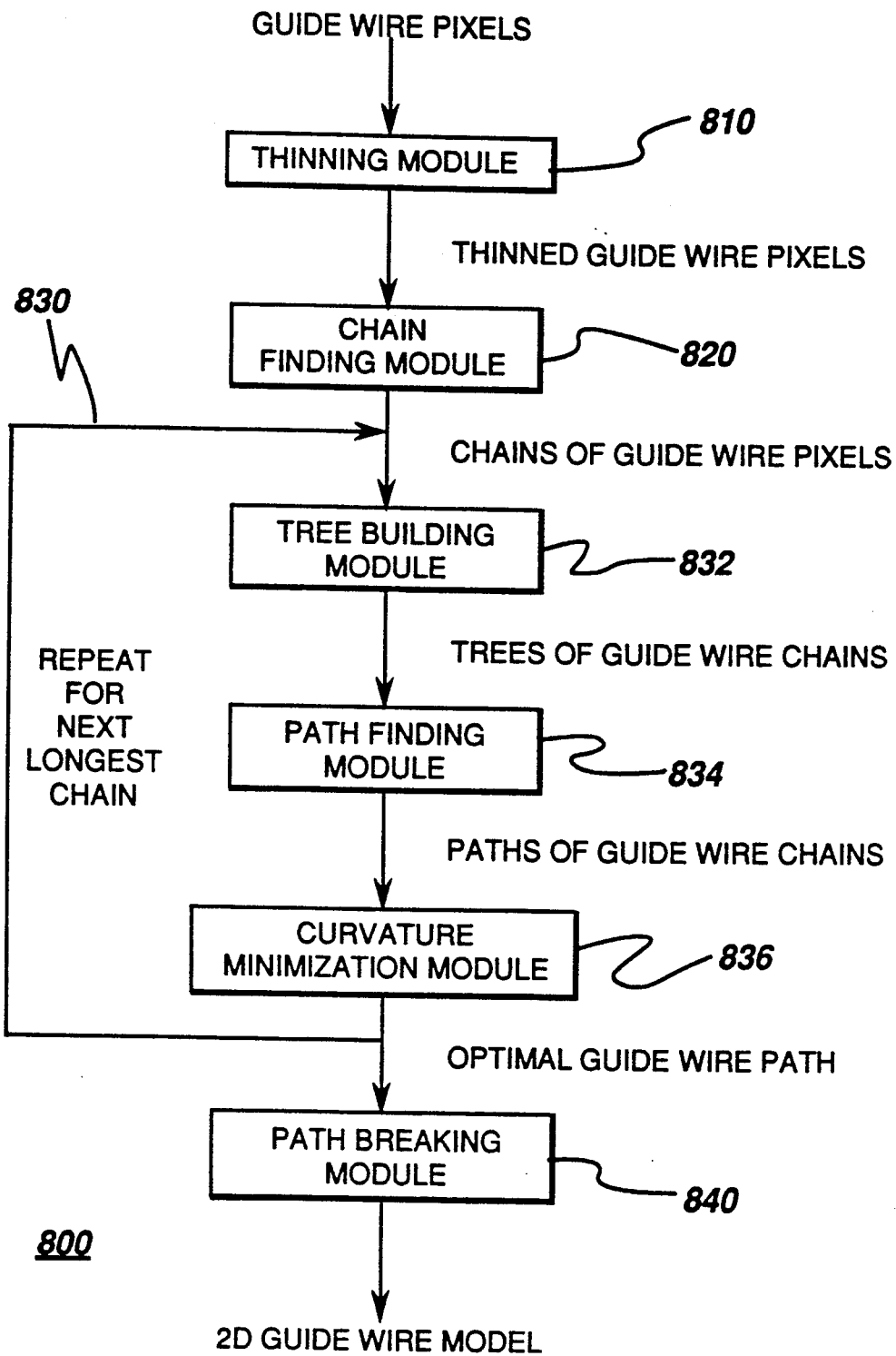
FIG. 8 is a system design diagram for the two-dimensional model creation sub-module.

FIG. 8 shows a two-dimensional model creation module 800. The goal of the two-dimensional model creation module 800 is to construct a two dimensional model of the catheter guide wire in the image plane. This is accomplished by several smaller modules shown in FIG. 8. The image is first thinned at block 810 so that all the lines in the image are only one pixel wide. Then, chains of pixels are identified at 820. Next, a set of longest connected paths is compiled from which the path with the least amount of curvature is selected (loop 830). Finally, this optimal path is broken into segments at 840 (based on local curvature) yielding a set of ordered vertices which can be saved as the two-dimensional catheter guide wire model in the image plane. Each of these modules will be described in detail in the following sections.

The first step 810 in two-dimensional model creation is thinning the peak image pixels in such a way that the genus of the image remains unchanged. The genus of an image is defined as the number of separated regions in an image. The neighbors of each pixel are scanned to determine if removing the pixel (setting it to the background color) will change the genus of the image. If removing the pixel will change the genus or if the pixel is an endpoint of a chain of pixels, then the pixel remains unchanged; otherwise, it is removed. This thinning process repeats until no pixels may be removed from the image.

Figure 9:
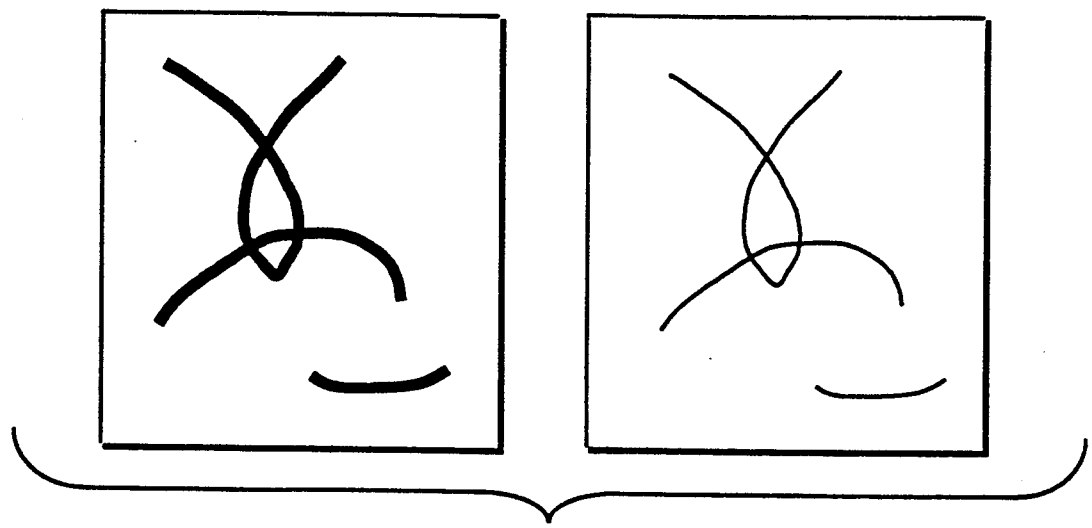
FIG. 9 illustrates thinning of a test image.

FIG. 9 shows two enlargements of a test image; one before thinning (on the left) and one after thinning (on the right). The square blocks in the thinned image on the right represent one pixel. Thinning the peak image is necessary for the chain finding module to function properly.

Referring again to FIG. 8, the pixels in the thinned peak image must be ordered into chains of pixels at block 820. This algorithm first examines the eight neighbors of each "on" pixel (not the background color) and counts the number of "on" neighbors of that pixel. If a pixel has two neighbors it is designated as a normal pixel; otherwise the pixel is designated as a juncture pixel. Therefore, ends of chains and intersection points become juncture pixels.

Figure 10:
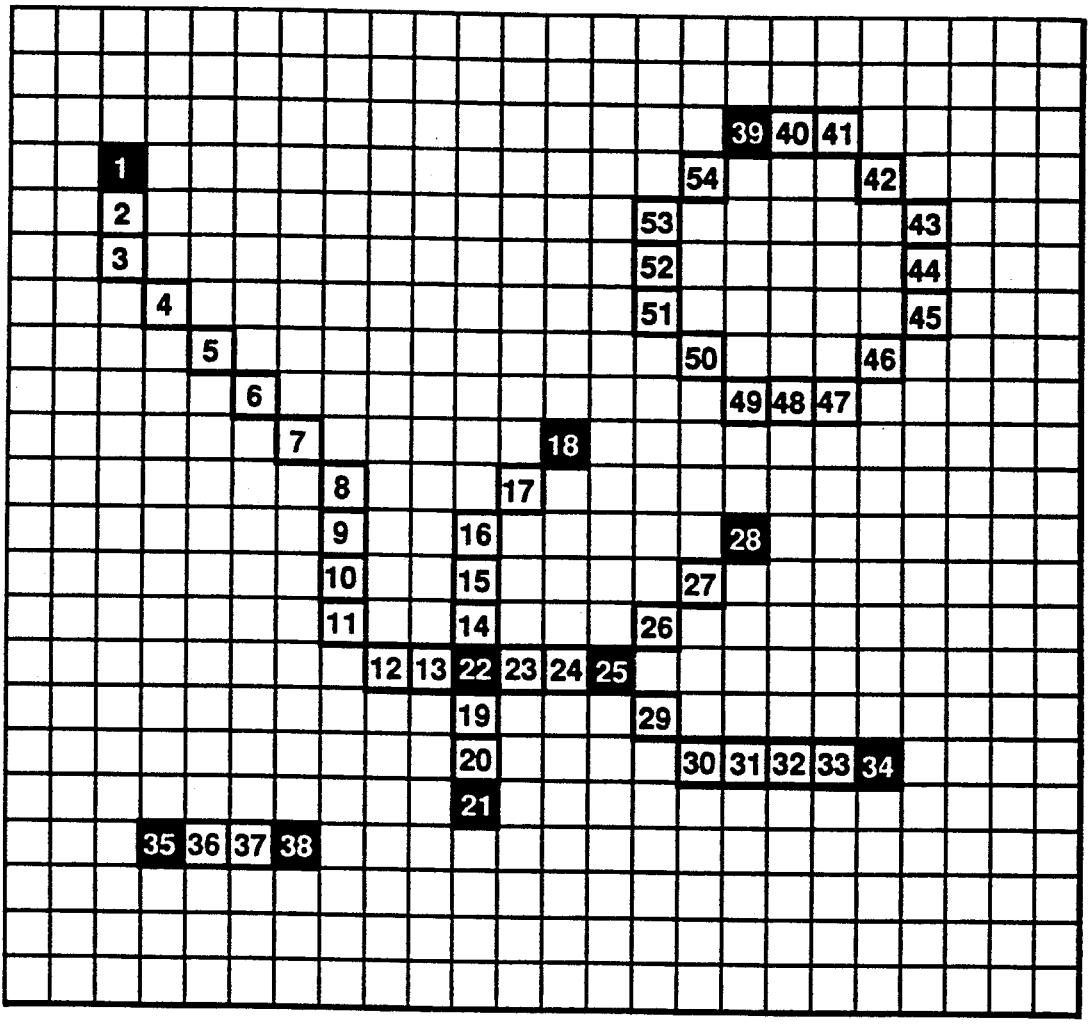
FIG. 10 illustrates chains of pixels in a test image.

FIG. 10 shows a small portion of a binary peak image; each box represents a pixel and the number inside of each box indicates its identification number. Normal pixels have black numbers in white boxes, juncture pixels have white numbers in black boxes, and background pixels have no numbers. In the chain finding module 820 in FIG. 8, chains are formed by traveling from one pixel to another starting at a juncture and ending at a juncture. The starting juncture pixel is designated the head of the chain and the ending juncture pixel is designated the tail of the chain. After all juncture pixel neighbors are processed, any remaining pixels are designated as being members of cycles; these chains of pixels do not contain any junctures. These pixels are processed in a special way. Within each cycle a random pixel is chosen to become a juncture pixel. At this point these cycles can be treated as the non-cyclic chains and traversed in the same way, from juncture to juncture (the starting and ending junctures are the same juncture; thus, the head and the tail of the chain are identical). The circle of pixels in the upper right hand corner of FIG. 10 exemplify a cycle. Using this algorithm, eight chains would be found in the image in FIG. 10; the chains are listed under the grid.

Referring again to FIG. 8, steps 832-836 find a group of chains which form the optimal path corresponding to the catheter guide wire. Here, optimal is defined as the longest semi-connected group of chains with the minimum curvature (semi-connected will be defined below). This is accomplished in three parts: tree building 832, path finding 834, and curvature minimization 836. In the tree building module 832, the proximity relationships between chains is computed by organizing the chains into a tree-like structure. This is necessary because the peak finding module usually does not yield a continuous chain of pixels which corresponds to the catheter guide wire. Therefore, chains whose endpoints are semi-connected to each other become candidates for being members of the two-dimensional model of the guide wire.

A tree is comprised of a number of nodes. A node can have one parent and a number of children. There are three types of nodes: roots, which have children but not a parent, regular nodes, which have children and a parent, and leaves, which do not have children but do have a parent. In this implementation, each node corresponds to a chain in the image. The tree building process starts by first finding the longest chain from the chain finding module. This chain will serve as the root node for two trees: one tree connected to its head pixel and another tree connected to its tail pixel.

Figure 11:
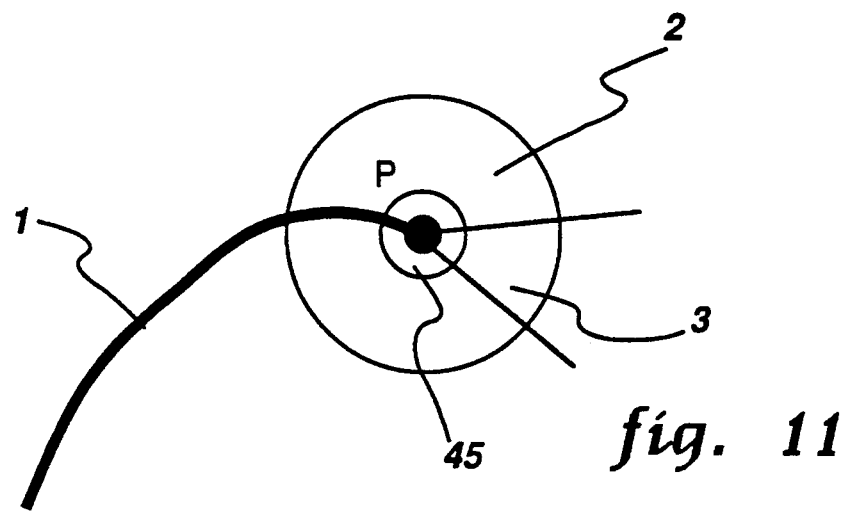
FIG. 11 is an illustration of semi-connected chains.

Building a tree is a simple recursive process which starts from a chain and works until there are no more chains that can be processed. Before the tree building process is described, the definition of "semi-connected" is supplied. FIG. 11 shows a typical scenario. The thick black line represents a chain of pixels (chain 1); the end of the chain marked by a filled black circle (pixel P) represents the pixel against which other chains are compared. Two larger circles surround tis endpoint. The smaller circle forms the boundary of the principle search region. If any other chain endpoint lies in this region, it is semi-connected to chain 1. The larger circle represents the secondary search region. If the endpoint of any other chain lies in this region (but not in the principle search region) it is semi-connected to chain 1 only if it also lies in the region bounded by the two rays emanating from P. The rays are chosen such that the bisecting ray between the two rays is parallel to the direction of the end of chain 1. In this implementation the radius of the principle search region is five pixel units, the radius of the secondary search region is three times the radius of the principle search region, and the angle between the rays is one radian. Only if a chain's endpoint lies in either of these two regions is it a candidate for becoming a child of chain 1. Thus, while chains 3 and 4 might become children of chain 1, chain 2 cannot.

Figure 12A:
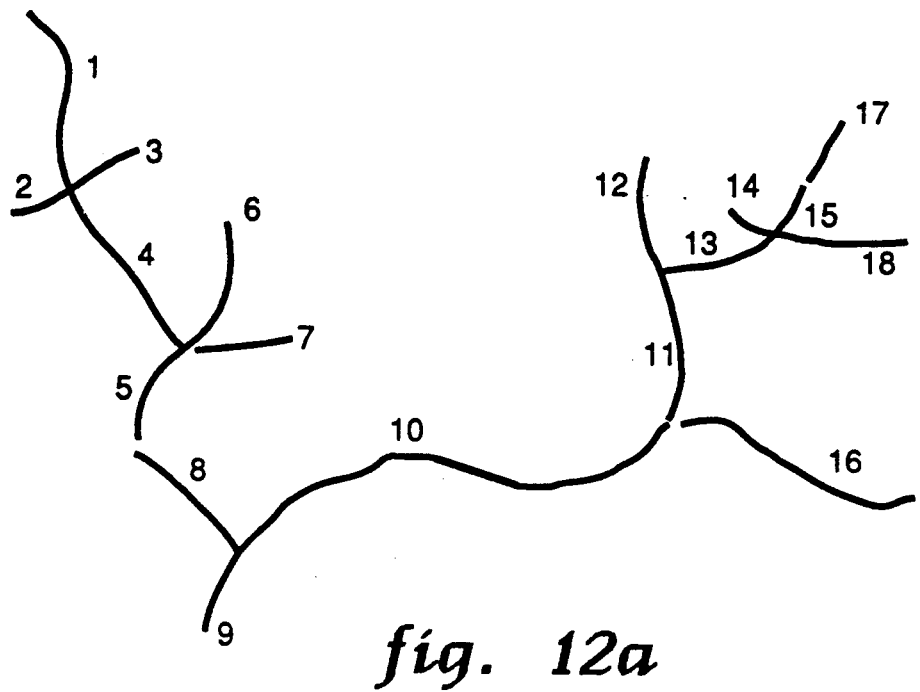
FIGS. 12a-12c illustrate tree building on a test image.
Figure 12B:
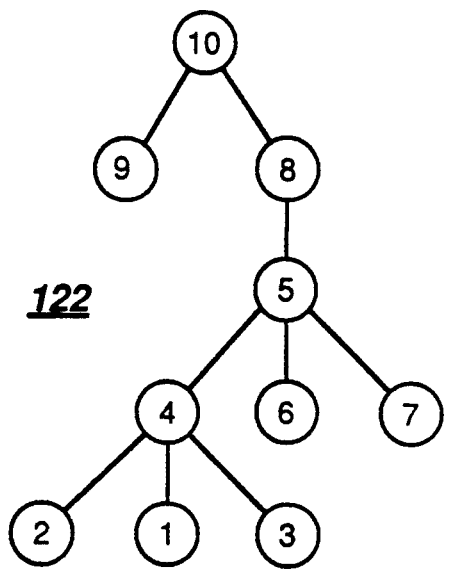
Figure 12C:
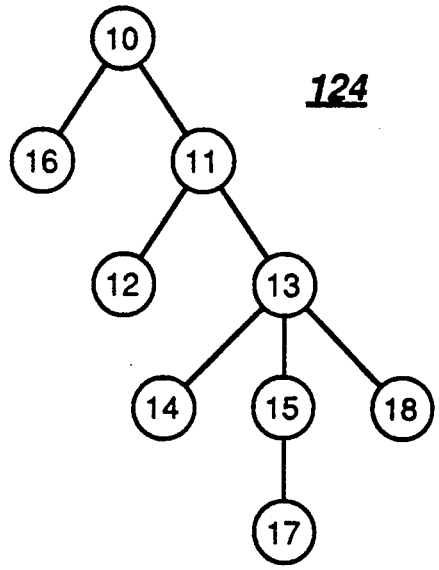

A few examples of tree building will explain the process. Examples of the tree building process on a test image is shown in FIG. 12. The chains are shown in FIG. 12a and the two resulting trees, one for the head pixel of the longest chain and one for the tail pixel, are shown in FIGS. 12b and 12c respectively. For simplicity, all chains which are relatively close to each other are considered to be semiconnected. In the trees 122 and 124, child nodes are shown in the tree below their parent node and the numbers inside the nodes of the trees designate the chain to which the node corresponds. Chain 10 is the longest chain in the image so both root nodes correspond to chain 10.

Figure 13:
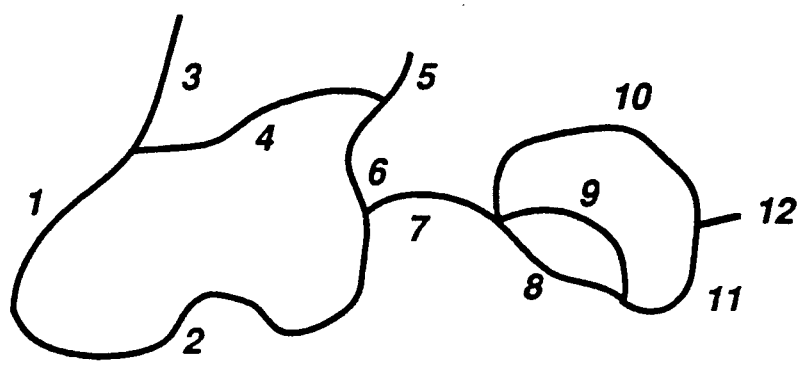
FIG. 13 illustrates a complex test image.
Figure 14A:
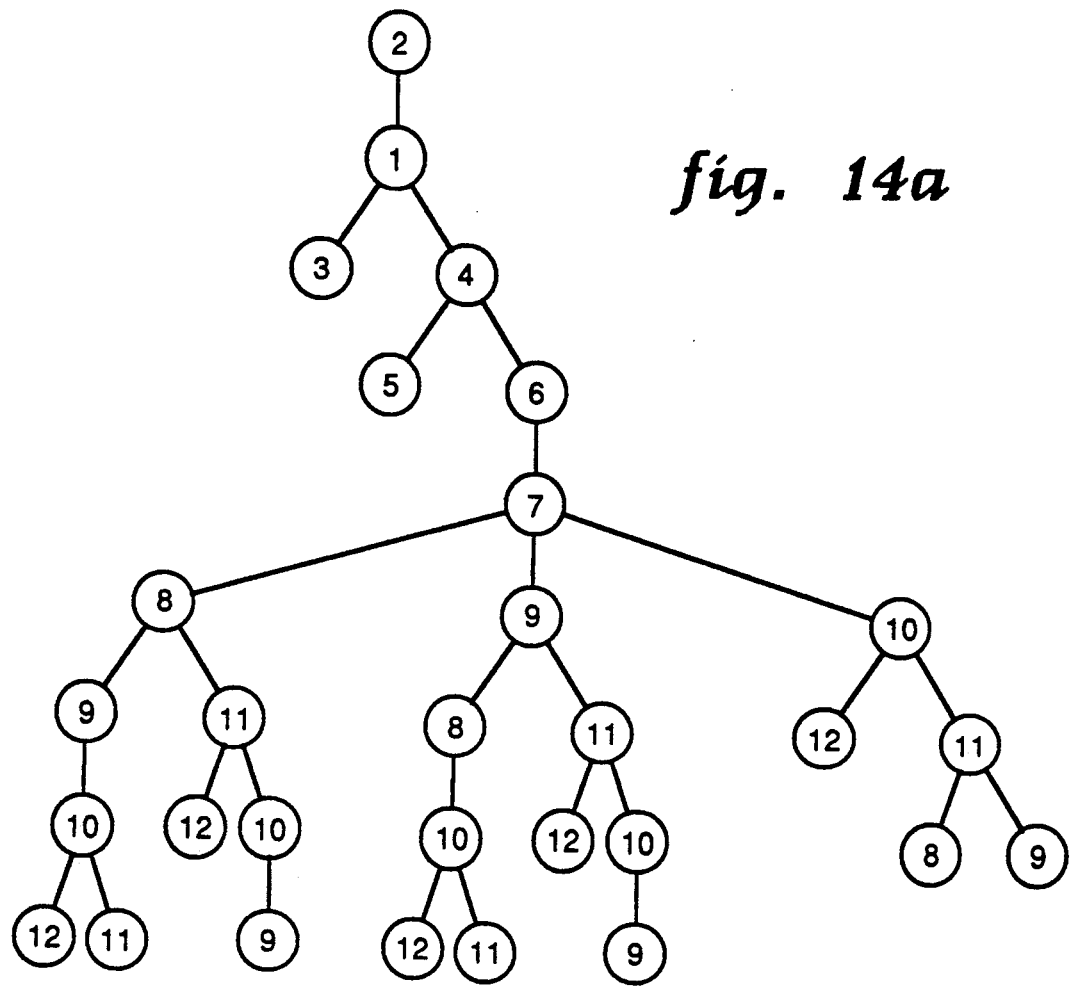
FIGS. 14a-14b illustrates tree building on a complex test image.
Figure 14B:
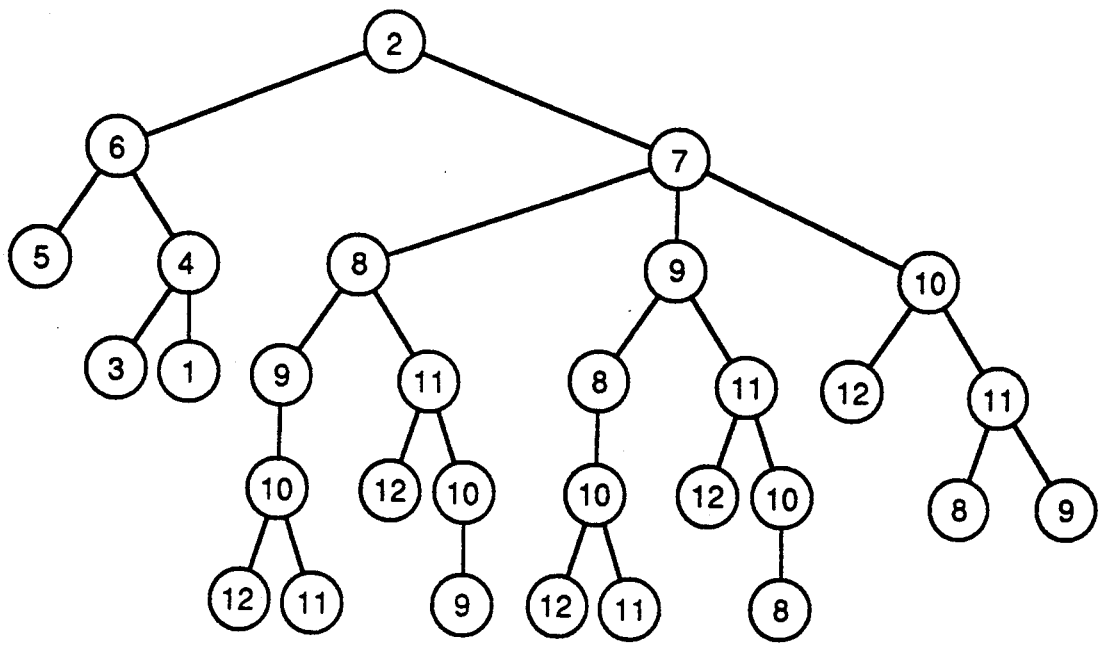

In the next example, a more complex tree building example is shown. FIG. 13 shows an image with fewer chains (12 compared with 17 in FIG. 12a) but much more complex trees (shown in FIGS. 14a-14b). The reason for this increased complexity is that the two trees formed from the endpoints of the longest chain (chain 2) are not disjoint sets; many chains appear in both trees. Also, some of the chains form loops which further complicate the process. This figure shows that there is one more constraint on the possible children of a chain in addition to being semi-connected. If chain B is semi-connected to chain A but chain B is an ancestor of chain A (parent, grandparent, etc.) then chain B cannot be a child of chain A. This prevents infinitely deep trees from forming. In the figure, once chain 9 has been designated as a child of chain 8, chains 8 or 7 cannot be children of 9 even though they are semi-connected to chain 9.

After both trees have been constructed, the longest, valid path through the nodes of the trees is discovered. This is accomplished by performing a depth first search on both trees (head tree and tail tree) and testing the path between every leaf node in one tree to every leaf node in the other tree for length and validity. A path is invalid if a chain appears twice in the path (of course, the root chain can appear in both trees). In FIG. 12a, computing the paths is relatively simple. The upper portion of FIG. 15 shows some of the 30 paths generated by these trees in the order that they are generated; the letter at the beginning of the path indicates whether the path is valid (V) or invalid (I). The lower portion of FIG. 15 shows some of the 182 paths generated for the complex example in FIG. 13. The length of the valid paths are computed by summing together the lengths of their component chains. This longest path (or paths) is then checked by the curvature minimization module.

Figure 16:
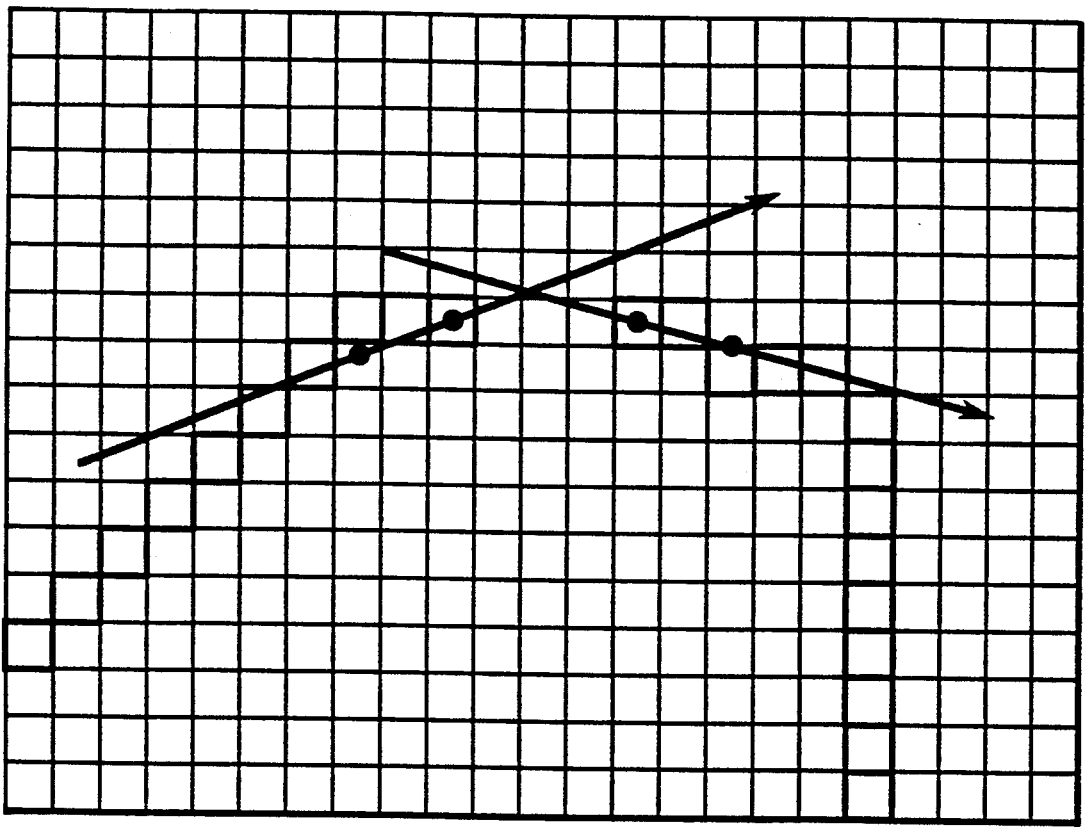
FIG. 16 illustrates angle calculation between two drains.

Referring again to FIG. 8, in the curvature minimization module 836, the curvature of all the longest paths is computed to determine which is the optimal path. The curvature of a path is the sum of the difference in angle between adjacent chains in the path. FIG. 16 shows how the angle between two chains is computed. The direction of an endpoint of a chain (shown as large arrows in the figure) is computed by calculating the average position of the N pixels closest to the endpoint of the chain (N=5). Then, the x and y values of the endpoint are subtracted from this average value to obtain a direction vector. The angle between the direction vector of one chain and the direction vector of the next chain defines the angle between two chains. Of the longest paths, the path with the lowest total curvature is designated the optimal path. This path is used by the path breaking module to compute the two-dimensional model of the guide wire.

As shown by loop 830 in FIG. 8, the method now scans all the chains to find the next longest chain and starts the tree building process again. The best path is stored in a global location so that when the new optimal path (derived from using the next longest chain as the root node for the head tree and tail tree) is computed it can be compared against the old optimal path. If the new optimal path is longer than the old optimal path then the new optimal path becomes the global optimal path. This process iterates until all chains are used as roots, or a predefined limit is reached.

Figure 17:
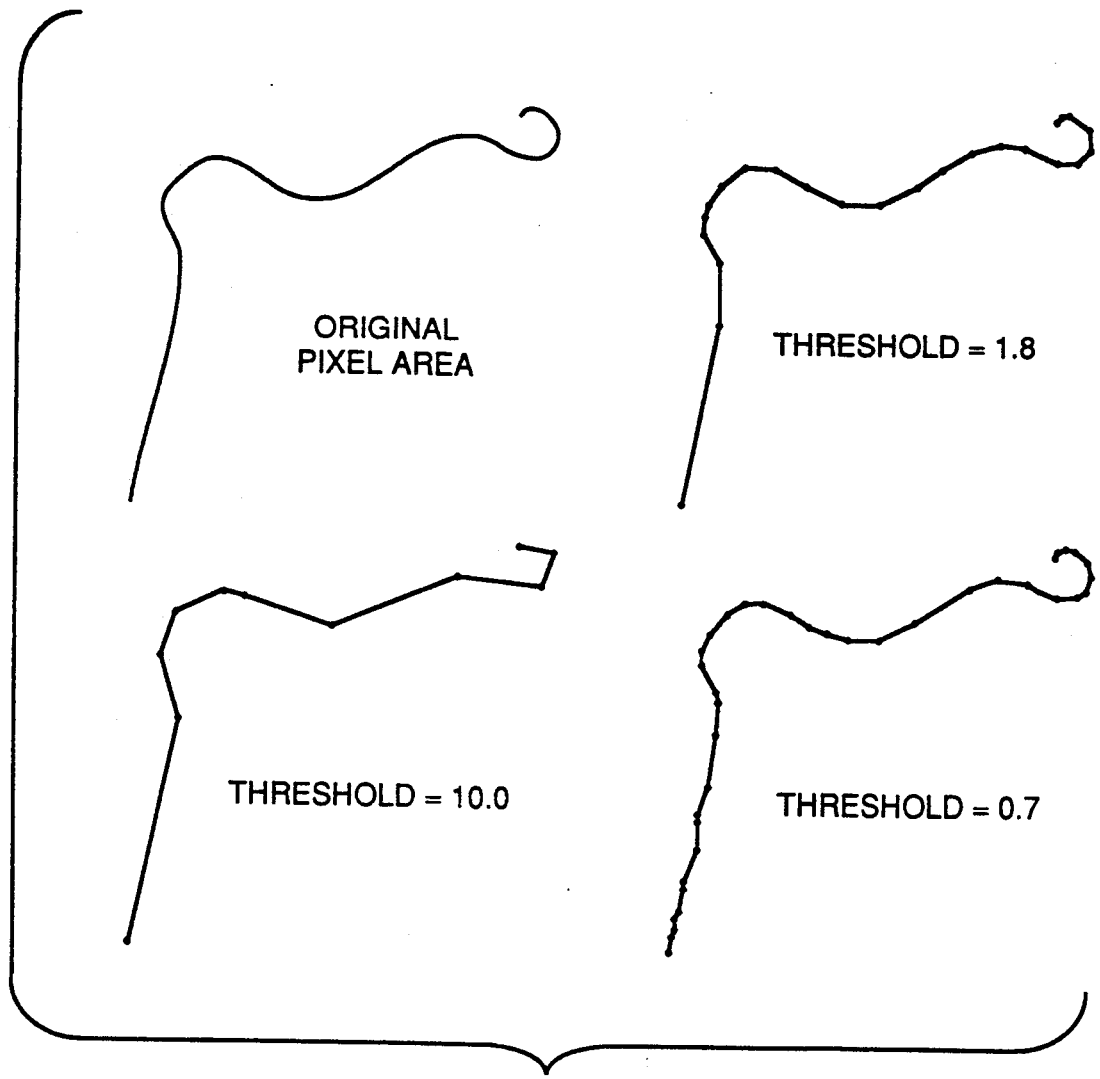
FIG. 17 illustrates the effect of varying thresholds on two-dimensional model complexity.

Finally, after the optimal path of chains has been found, the path is converted into a two-dimensional model at block 840. The two-dimensional model of the chains of pixels in the optimal path is a compact representation of the whole path; the model conveys the essence of the path without enumerating every pixel in the path. The representation of the two-dimensional model used in the present invention, is a simple, ordered, set of pixels which, when connected by lines, approximates the original path. Before any further processing, the pixels in the chains of the optimal path are dumped (in order) into an linear array of pixels. The array of pixels are recursively split into smaller and smaller segments until a certain threshold is reached; this threshold specifies the maximum distance (in pixel units) between the array of pixels and the two-dimensional model. If the distance between the line segment of the two-dimensional model and the array of pixels exceeds the threshold, the segment is split into two segments and the process is then invoked on the smaller segments. FIG. 17 shows the effect of different thresholds on the two-dimensional model created from the array of pixels. Higher thresholds will give coarse two-dimensional models but extremely small thresholds will yield two-dimensional models which too closely match the pixel grid. The dots in FIG. 17 correspond to vertices of the two-dimensional model and the lines connecting the blocks represent the ordered edges of the two-dimensional model. A threshold of three pixel units yields reasonable models.

The constrained backprojection module (240 in FIG. 2) is now described. The purpose of this module is to compute the three dimensional location (position and orientation) of the catheter guide wire within the three-dimensional vascular map. This information is then conveyed to the radiologist by highlighting the guide wire location in the three-dimensional vascular map. Using this information, the radiologist can guide the catheter more easily to the desired location.

One method for backprojection involves using the X-ray source and image intensifier angles relative to the patient position to define a frustrum like volume within the patient. There should be at least a rough correspondence between patient position/orientation and the position/orientation of the 3D vascular model. The frustrum selects out a corresponding portion of the 3D vascular map which should be roughly aligned with the actual patient position/orientation. A number of "forward" 2D projections of the 3D vascular map are then formed in a way that mimics the actual X-ray/fluoroscope apparatus. Each of these forward projections would need to be checked against the current fluoro 2D image. The fluoro image will be called the template image and any of the 2D forward projection images the test image. All possible ways in which the template can be matched against features of a test image must be determined. The matching is carried out on a feature by feature basis and not on a pixel by pixel basis. Only the most salient features are extracted and matched first (such as abrupt changes of curvature, or places where the artery/guide wire crosses over itself). All tentative matches are noted. At least six feature points are needed to determine the translation/rotation transformation. If scale can vary then at least one additional correspondence is required.

After this is done for all forward images, it is necessary to pare down the list of potential matches to one. This is done by clustering the possible matches. Since there really is only one correspondence, there will be more list entries for the "correct" roll/pitch/yaw/x-/y/z scale value. Others can be discarded.

If the view is "degenerate" (i.e., looking down the tube one can not determine how far along the tube the wire is), then uncertainty exists as to exact tip position. Because of the degenerate view problem, the actual distance of the tip along a relatively straight section of artery may not be determinable. This is where extra information or constraint information may be used. One approach would use a mechanism that measures the amount of guide wire in a patient at all times. By comparing path length along the 3D vascular map with measured guide wire length, one can determine actual tip position. If the tip is in the vicinity of a branch, or if the degenerate view does not supply much information as to actual guide wire shape, then constraint information such as a mechanical bending model of the guide wire tip or general anatomical knowledge can help accept or reject hypothesized matches. The most valuable information is the tip position and tip motion determined in the previous frames.

To summarize, a set of features in the template image when matched successfully against a test image, determines the actual 3D transformation matrix. The fine details and extra degrees of freedom are determined by extra information, multiple views, and constraints. The number of forward projections would depend on the degree of uncertainty of actual patient orientation relative to the apparatus and the degree of uncertainty of alignment of the 3D vascular map and the actual patient position. The 3D model might be projected forward at nine angular spacings of 0, $-5$ degrees and $+5$ degrees x (azimuth) and y (elevation) (all combinations for x and $y = 3^2 = 9$ 2D images).

Once the exact correspondence between template and 3D vascular map is known, the real-time 3D graphics display could be changed to reflect this geometric data. As an example, if the 3D vascular map is displayed with all pathways shown in pale green glass-like tubes and displayed at an orientation preferred by a physician, the tubes that are known to contain the catheter guide wire are changed to yellow. If a given tube is partially filled, then only a portion of its length is changed from green to yellow. A vascular tube is specified by knowing the xyz positions of the last branching and the xyz positions of the next branching and the space curve that defines the axis of the tube, which could be a straight line or spline.

The entire system is designed to continuously and efficiently interface with the physician allowing him to manipulate and alter the contents of the display. For example, using a trackball he can view the three-dimensional vascular map from alternate vantage points or magnifications. Thus, the physician could obtain a view from an alternate direction without necessarily having to physically alter the position and orientation of the X-ray/fluoroscope system.

An important benefit of this system is the elimination of the need to inject contrast media into the patient. Patient sensitivity to the contrast dye used in IR procedures varies greatly. Large doses can have undesirable and possibly toxic side effects on the patient; thus it is desirable to minimize the amount of dye used. The physician uses the dye to temporarily opacify the vessel to verify his position. He needs to do this at many points during the procedure. The proposed system would not need to periodically inject dye to determine position. The guide wire is readily visible in the fluoroscope image by virtue of its natural opacity to X-rays. The vascular map supplies the vascular network reference data. Thus, assuming possession of the map, no additional dye is required.

The system could also be used in a hierarchical manner. In neurological procedures in the brain, the vascular diameter can become very small at the furthest reaches. In general, it may not be possible to acquire a map with sufficient resolution initially. The approach used in these cases would be to start with an initial "course" map, navigate to a convenient waypoint and then pause to acquire sufficient data to generate a second more detailed local map. In general one might use multiview reconstruction techniques based on a dye injection and multiview planar X-ray images at this time to generate the local map rather than transfer the patient to a CT or MR scanner. In principle, it would be possible to perform the IR procedures within the bore of a CT or MR machine, thus giving the possibility of acquiring the more detailed local maps when required. Regardless of how the subsequent three-dimensional map is acquired, the new vascular map is "spliced into" the existing network of maps and navigation resumed. In principle, this could occur any number of times.

While the present invention has been described with respect to specific embodiments, many modifications, variations, alterations, substitutions, and equivalents will be apparent to those skilled in the art. Accordingly, the invention is to be considered as limited only by the spirit and scope of the appended claims.

What is claimed is:

1. A method for providing real-time navigation assist for Interventional Radiological procedures in a fluoroscopic examination system including a fluoroscope, a three-dimensional display device, an image digitizer with storage capability, and a three-dimensional model of a patient's vascular system, said method comprising the steps of:

extracting pixels in a digitized fluoroscopic image corresponding to the path of a catheter within the vascular system of a patient undergoing an IR procedure;

backprojecting said catheter path into said three-dimensional model; and displaying a three-dimensional image on said three-dimensional display device, said image representing said catheter within said three-dimensional model.

2. The method of claim 1 wherein said backprojecting step comprises the steps of:

determining the approximate region of said three-dimensional model in which said catheter is traveling; and correlating the pathways in said region with said pixels.

3. A method for providing real-time navigation assist for Interventional Radiological procedures in a fluoroscopic examination system including a fluoroscope, a three dimensional display device, an image digitizer with storage capability, and a three-dimensional model of a patient's vascular system, said method comprising the steps of:

creating a binary peak image;

constructing a two-dimensional model of said catheter path from said binary peak image;

backprojecting said catheter path into said three-dimensional model; and displaying a three-dimensional image on said three dimensional display device.

4. The method of claim 3 wherein said constructing step comprises the steps of:

a) thinning said binary peak image;

b) organizing said thinned binary peak image into pixel chains;

c) organizing said pixel chains into first and second trees of pixel chains, wherein said first and second tree represent a first and second direction relative to the longest of said pixel chains and said first and second trees represent paths of semi-connected pixel chains;

d) searching said trees for longest valid paths through the nodes of said trees;

e) selecting a path with minimum curvature if no single valid path is longest;

f) repeating steps c–e using a next longest of said pixel chains in step c;

g) selecting a longest of the valid paths found in step d; and h) representing said longest valid path as a set of line segments.

5. An apparatus for providing real-time navigation assist for Interventional Radiological procedures in a fluoroscopic examination system including a fluoroscope, a three-dimensional display device, an image digitizer with storage capability, and a three-dimensional model of a patient's vascular system, said apparatus comprising:

means for extracting pixels in a digitized fluoroscopic image corresponding to the path of a catheter within the vascular system of a patient undergoing an IR procedure;

means for backprojecting said catheter path into said three-dimensional model; and means for displaying a three-dimensional image on said three-dimensional display device, said image representing said catheter within said three-dimensional model.

6. The apparatus of claim 5 wherein said backprojecting means comprises:

means for determining the approximate region of said three-dimensional model in which said catheter is traveling; and means for correlating the pathways in said region with said pixels.

7. An apparatus for providing real-time navigation assist for Interventional Radiological procedures in a fluoroscopic examination system including a fluoroscope, a three dimensional display device, an image digitizer with storage capability, and a three-dimensional model of a patient's vascular system, said apparatus comprising:

means for creating a binary peak image;

means for constructing a two-dimensional model of said catheter path from said binary peak image;

means for backprojecting said catheter path into said three-dimensional model; and means for displaying a three-dimensional image on said three dimensional display device.

8. The apparatus of claim 7 wherein said constructing means comprises:

a) means for thinning said binary peak image;

b) means for organizing said thinned binary peak image into pixel chains;

c) means for organizing said pixel chains into first and second trees of pixel chains, wherein said first and second tree represent a first and second direction relative to the longest of said pixel chains and said first and second trees represent paths of semi-connected pixel chains;

d) means for searching said trees for longest valid paths through the nodes of said trees;

e) means for selecting a path with minimum curvature if no single valid path is longest;

f) means for repeating steps c–e using a next longest of said pixel chains in step c;

g) means for selecting a longest of the valid paths found in step d; and h) means for representing said longest valid path as a set of line segments.

9. An apparatus for providing real-time navigation assist for Interventional Radiological procedures in a fluoroscopic examination system including a fluoroscope, a three-dimensional display device, an image digitizer with storage capability, and a three-dimensional mode of a patient's vascular system, said apparatus comprising:

a digital computer comprising means for:

extracting pixels, in a digitized fluoroscopic image, corresponding to the path of a catheter within the vascular system of a patient undergoing an IR procedure;

backprojecting said catheter path into said three-dimensional model; and displaying a three-dimensional image on said three-dimensional display device, said image representing said catheter within said three-dimensional model.

10. The apparatus of claim 9 wherein said digital computer comprises means for:

determining the approximate region of said three-dimensional model in which said catheter is traveling; and correlating the pathways in said region with said pixels.

11. An apparatus for providing real-time navigation assist for Interventional Radiological procedures in a fluoroscopic examination system including a fluoroscope, a three-dimensional display device, an image digitizer with storage capability, and a three-dimensional model of a patient's vascular system, said apparatus comprising:

a digital computer programmed to:

create a binary peak image;

construct a two-dimensional model of said catheter path from said binary peak image; and backproject said catheter path into said three-dimensional model; and means for displaying a three-dimensional image on said three-dimensional display device.

12. The apparatus of claim 11 wherein said digital computer comprises means for:

a) thinning said binary peak image;

b) organizing said thinned binary peak image into pixel chains;

c) organizing said pixel chains into first and second trees of pixel chains, wherein said first and second tree represent a first and second direction relative to the longest of said pixel chains and said first and second trees represent paths of semi-connected pixel chains;

d) searching said trees for longest valid paths through the nodes of said trees;

e) selecting a path with minimum curvature if no single valid path is longest;

f) repeating steps c–e using a next longest of said pixel chains in step c;

g) selecting a longest of the valid paths found in step d; and h) representing said longest valid path as a set of line segments.

* * * * *